United States Patent
Horton

(10) Patent No.: US 6,796,949 B2
(45) Date of Patent: Sep. 28, 2004

(54) SOCK FOR DETECTION OF PRESSURE POINTS IN FEET

(75) Inventor: James M. Horton, Charlotte, NC (US)

(73) Assignee: Charlotte-Mecklenburg Hospital Authority, Charlotte, NC (US)

( * ) Notice: Subject to any disclaimer, the term of this patent is extended or adjusted under 35 U.S.C. 154(b) by 40 days.

(21) Appl. No.: 10/149,566

(22) PCT Filed: Dec. 14, 2000

(86) PCT No.: PCT/US00/33892

§ 371 (c)(1),
(2), (4) Date: Oct. 7, 2002

(87) PCT Pub. No.: WO01/43638

PCT Pub. Date: Jun. 21, 2001

(65) Prior Publication Data

US 2003/0208143 A1 Nov. 6, 2003

Related U.S. Application Data

(60) Provisional application No. 60/170,816, filed on Dec. 15, 1999.

(51) Int. Cl.[7] .............................................. A61B 5/103
(52) U.S. Cl. ...................... 600/592; 600/587; 128/898; 2/239
(58) Field of Search ................................ 600/300, 549, 600/553, 556, 557, 587, 592; 33/511, 512; 2/239; 128/897, 898

(56) References Cited

U.S. PATENT DOCUMENTS 5,339,252 A * 8/1994 White et al. .................. 700/98
5,390,680 A   2/1995 Brenner
5,642,096 A * 6/1997 Leyerer et al. ........... 340/573.1
5,678,566 A   10/1997 Dribbon
5,682,617 A * 11/1997 Tumas ........................... 2/239
5,778,702 A * 7/1998 Wrightenberry ........... 66/178 R
6,493,958 B1 * 12/2002 Tadin ........................... 33/515

OTHER PUBLICATIONS

Hampton, George H., "Therapeutic Footwear for the Insensitive Foot", *Physical Therapy*, Jan. 1979, vol. 59, No. 1, pp. 23–29.

Rajeswaramma, Vermeriddi et al., "Pressure–Sensitive Stump Sock", *Archives of Physical Medicine and Rehabilitation*, Mar. 1973, pp. 142–144.

International Search Report.

* cited by examiner

*Primary Examiner*—Charles Marmor
(74) *Attorney, Agent, or Firm*—Alston & Bird LLP

(57) ABSTRACT

This invention provides a sock containing a coating material such as a coloring agent or dye, applied to at least a portion of the interior surface of the sock for sensing pressure points on a patient's foot to which the sock is fitted. The sock is placed on the patient's foot to cover preferably the entire foot, but at least the bottom portion thereof. The sock is removed after being worn for a period of time, and in those areas of the foot susceptible to pressure points, the coating material transfers from the interior of the sock and adheres to the foot in those points. The present invention is particularly applicable to a person having diabetic neuropathic feet wherein portions of the foot may be insensitive to pressure and therefore must be protected against pressure sores.

11 Claims, No Drawings

SOCK FOR DETECTION OF PRESSURE POINTS IN FEET

CROSS-REFERENCE TO RELATED APPLICATIONS

This application is a U.S.C. §371 National Stage Commencement of Application Ser. No. PCT/US00/33892, filed Dec. 14, 2000, which claims the benefit of priority of Provisional Application Ser. No. 06/170,816, filed Dec. 15, 1999, all of which are incorporated herein reference in their entirety.

BACKGROUND OF THE INVENTION

The present invention relates to a sock having means for the detection of pressure points on a foot of a patient having diminished sensation in the foot and to a method for sensing diabetic neuropathic foot disease. More specifically, the present invention relates to a sock containing a coloring agent or dye that is removed from the sock onto a wearer's foot by the pressure points.

Diabetic neuropathic foot disease is the most common cause of amputation in the United States. The problem is that a diabetes patient can suffer a partial or complete loss of feeling in the lower extremities and especially in the foot. A healthy person starts to feel pain when subjected to continuous local pressure and therefore shifts their body automatically to lessen the discomfort, but patients having a sensatory loss are deprived of this protection and are therefore common victims of pressure sores and open wounds which can become ulcerated.

It is therefore desirable to detect the pressure points in the foot to prevent pressure sores and wounds so that a patient who might not be able to recognize existence of a pressure point inducing condition can get off of his or her feet to eliminate the condition or to take such other preventative measures as may eliminate or reduce the condition.

Devices are known in the prior art for indicating to persons having diminished sensation in the foot that their feet are being exposed to excessive stress conditions. Many of these devices include shoes which detect excess pressure through a force sensor and signals the wearer of the existence that a threshold pressure has been reached. Examples of such devices are described in U.S. Pat. No. 5,566,479, U.S. Pat. No. 4,610,253, U.S. Pat. No. 4,647,918 and U.S. Pat. No. 5,642,096. The difficulty with such devices is that they are expensive and cumbersome to wear. Accordingly, it is desirable that there be provided a method for conveniently detecting the pressure points in the foot of a patient with diminished sensation.

SUMMARY OF THE INVENTION

An object of the present invention is to provide a sock having means for the detection of pressure points on a foot of a patient having diminished sensation in the foot.

Another object of the present invention is to provide a sock containing a dye which, when the sock is worn, at least a portion of the dye is transferred from the sock and adheres to pressure points of a patient's foot.

Yet another object of the present invention is to provide a method for sensing diabetic neuropathic foot disease.

According to one aspect of the present invention, there is provided a sock for detecting pressure points on a foot of a patient being diagnosed for diminished sensation in the foot. The sock has a coating material applied to at least a portion of the interior surface of the sock so that when the patient wears the sock, the coating material transfers from the interior surface of the sock to the foot at the pressure points.

According to another aspect of the present invention, a method is provided for detecting pressure points on a foot of a patient being diagnosed for diminished sensation in the foot. The method includes fitting a sock of this invention to the foot to be examined, having the patient wear the sock for a period of time, and removing the sock to determine the points of the foot where the removable coating material has been transferred to the foot. Generally speaking, the sock will need to be only worn a short period of time preferably from 10 minutes to 30 minutes in order for the dye to be transferred from the sock to the pressure points on the patient's foot.

The present invention is particularly useful in diabetes patients. The socks of this invention can be worn with shoes on. Thus the patient can perform normal activities while pressure points can be detected in real time. Once the pressure points in the patient's feet are detected, the patient may then be treated to prevent the development of sores or ulcers. Conventionally, the patient's shoes can be altered to ease the pressure in the affected portion of the foot.

Further features and advantages of the invention will be apparent from the description below.

DETAILED DESCRIPTION OF THE INVENTION

While the invention will be described in connection with preferred embodiments, it should be recognized and understood that the following description is not intended to limit the invention to the preferred embodiments. On the contrary, the invention is intended to include all alternatives, modifications and equivalents which may be determined to be within the spirit and scope of the invention as disclosed and claimed below.

This invention provides a sock for detecting pressure points on a patient's foot. The sock is normally sized to substantially conform to the shape of a human foot with a sufficiently snug fit to allow transfer of coloring agent or dye to a pressure point. As used herein, the terms "coloring agent" and "dye" are intended to mean those materials that can move from or be transferred from the sock to the foot to indicate a pressure point. The terms "coloring agent" and "dye" are used collectively as "coloring material." At least a portion of the interior surface of the sock is coated with a coloring agent or dye such that when the patient's foot wears the sock, the coloring agent or dye transfers from the interior surface of the device to the foot at the pressure points as a detectable marking. The amount of the coating material transferred is determined by the pressure the foot exerts on the interior surface of the sock. Preferably, the amount of transfer under normal ordinary non-harmful low pressure is sufficiently different from the pressure exerted under harmful, ulceration-causing pressure. Most preferably, the transfer of the coating material is only detectable when the pressure is excessive. By "excessive" it is intended to mean that the pressure is sufficiently high so as to adversely affect the pressure points, i.e., the location on the foot withstanding the pressure, for example causing sores or ulceration.

Many removable coating materials can be used to achieve the above goals, as will be apparent to a skilled artisan in the chemical art. The materials should not cause any substantial adverse effect to the foot and the sock of this invention. One embodiment of the coating material for use in the socks of this invention is in the form of a powder. However, preferably, the coating material is in a paste-like form. The coating material includes, e.g., zinc oxide, titanium dioxide, or magnesium oxide and the like. When a paste containing the coating material is desired, non-toxic oils, glycerin, glycols, vaseline and the like can be mixed with the solid materials. An example of the coating material may be a paste composition including an oil (animal, vegetable, or mineral oils) or glyceride in admixture with a coloring agent powder or a powder of zinc oxide, titanium dioxide, or magnesium oxide and the like. For example, the paste can be made of about 1 to about 2.5 parts of glyceride and about 1–5 parts of the above powder blended together.

In another embodiment of the present invention, the coating material includes a coloring agent such as food coloring agents, water soluble dyes, dyes soluble in an organic solvent (e.g., oil), and fluorescence dyes, and a suitable thickening agent in admixture. The coating material formulation may also include a liquid glycol such as ethylene glycol, propylene glycol, glycerin, polyethylene glycol or the like.

The coating materials can be applied to the interior surface of the device by any suitable methods. Preferably, in the case of a paste, it can be applied as a spray and then allowed to dry. For example, the paste can be loaded into a conventional aerosol spray can with a suitable propellant such as butane. The paste can be applied to the device by spraying the coating materials from the aerosol to the interior surface of the device. Optionally, the applied coating material becomes substantially dry after the application. In a preferred embodiment, conventional denture indicator pastes such as Hydrent® denture indicator paste and Occlude® aerosol indicator marking spray both of which are commercially available from Pascal Co. Inc., Bellevue, Wash. are used.

In a preferred embodiment, the device comprises a sock having a coating material applied to at least a portion of the interior surface of the sock. The sock can be any conventional sock made of any textile or non-textile materials. In a preferred embodiment of the invention, there is provided a sock having at least two layers and most preferably the sock is a double-layered sock. The inner layer is impregnated or coated with a dye that changes color when it becomes acidic and the outer sock layer contains an acid such as, for example, citric acid. When pressure is applied to the dye containing area in the sock, pressure is applied against both layers of the sock and the dye is caused to react with the acid and changes colors when the dye turns acidic, thereby indicating a pressure point. In another embodiment of the invention, the dye may be contained on a pressure sensitive film and adhered to the interior of the sock.

The sock of this invention can be useful in detecting pressure points on a patient's foot with diminished sensation. The invention is especially useful in diabetic patients. With diabetic neuropathic foot disease, diabetes patients often lack sufficient sensation to feel excess pressure on the feet. Often such excessive pressure is exerted by unfit shoes, or is because of abnormal growth of tissue in the feet. If the excessive pressure continues, foot sores or ulceration can develop and aggravate due to continued excessive pressure or rubbing. Often ultimately this leads to the necessity of amputation.

With the present invention, for example, the sock having the coated materials applied onto the interior surface thereof is worn by a patient's foot which is diagnosed of or suspected of diminished sensation. The sock is worn just like a normal sock thus does not interfere with the patient's normal life. For a period of time, which can be as short as 10 minutes to 30 minutes depending upon which dye is used up to a longer time say from one day up to several days. After that time, the sock is removed from the foot and both the foot and the sock are examined. The transfer of the coating material to the foot is usually associated with high pressure points. Thus, by examining the sock and the foot, high pressure points can be determined. Accordingly, the high pressure points can be treated with suitable medicines or devices to inhibit or prevent sores or ulceration. Alternatively, the shoes of the patient can be altered based on the location of the high pressure points to better fit the foot.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A sock for detecting pressure points on a foot of a patient being diagnosed for diminished sensation in a foot comprising, a sock containing a coating material selected from the group consisting of zinc oxide, titanium dioxide and magnesium oxide applied to at least a portion of the interior surface of the sock so that when the patient wears the sock, the coating material transfers from the interior surface of the sock to the foot at the pressure points.

2. The sock of claim 1, wherein said coating material is a paste.

3. The sock of claim 1 wherein said sock is a double layered sock having an inner layer and an outer layer.

4. A sock for detecting pressure points on a foot of a patient being diagnosed for diminished sensation in a foot comprising, a sock containing a coating material selected from the group consisting of water soluble dyes, oil soluble dyes, food coloring, acid activated dyes and fluorescent dyes applied to at least a portion of the interior surface of the sock so that when the patient wears the sock, the coating material transfers from the interior surface of the sock to the foot at the pressure points.

5. The sock of claim 4, wherein said coating material comprises a liquid glycol, a thickening agent and a coloring agent.

6. A sock for detecting pressure points on a foot of a patient being diagnosed for diminished sensation in a foot comprising, a sock containing a coating material applied to at least a portion of the interior surface of the sock so that when the patient wears the sock, the coating material transfers from the interior surface of the sock to the foot at the pressure points, wherein said sock is a double layered sock having an inner layer and an outer layer, and wherein said inner layer contains a dye that changes color when contacting an acid and said outer layer contains an acid that causes the dye in said inner layer to change color upon contacting the dye.

7. A method for detecting pressure points on a foot of a patient being diagnosed for diminished sensation in the foot, comprising:

providing a sock having a coating material applied to at least a portion of the interior surface of the sock;

fitting said sock to the foot of said patient;

wearing said sock for a time sufficient for at least a portion of said coating material to transfer from the interior surface of the sock to the foot at the pressure points; and removing said sock and determining the points of the foot where the removable coating material has been transferred to the foot.

8. The method according to claim 7 wherein said coating material is selected from the group consisting of zinc oxide, titanium dioxide and magnesium oxide.

9. The method according to claim 7 wherein said coating material is selected from the group consisting of water-soluble dyes, oil soluble dyes, acid activated dyes, fluorescent dyes and food coloring.

10. The method according to claim 7 wherein said sock is a double layered sock having an inner layer and an outer layer, wherein said inner layer contains a dye that changes color when contacting an acid and said outer layer containing an acid that causes the dye in said inner layer to change color upon contacting the dye.

11. A method for sensing diabetic neuropathy in a foot having pressure points comprising:

providing a sock containing a dye applied to the interior surface of said sock;

fitting said sock to the foot of a patient;

wearing said sock for a period of time sufficient for at least a portion of said dye to rub onto the foot of a patient at said pressure points;

removing said sock after said period of time and determining the areas of the foot where the dye has adhered to the foot; and treating said pressure points of the foot.

* * * * *